(12) United States Patent
Lee

(10) Patent No.: US 9,649,161 B2
(45) Date of Patent: *May 16, 2017

(54) STEREOTACTIC POSITIONING GUIDE APPARATUS

(71) Applicant: Choon Kee Lee, Denver, CO (US)

(72) Inventor: Choon Kee Lee, Denver, CO (US)

( * ) Notice: Subject to any disclaimer, the term of this patent is extended or adjusted under 35 U.S.C. 154(b) by 656 days.

This patent is subject to a terminal disclaimer.

(21) Appl. No.: 14/160,492

(22) Filed: Jan. 21, 2014

(65) Prior Publication Data

US 2015/0202010 A1 Jul. 23, 2015

(51) Int. Cl.
| | | |
|---|---|---|
| A61B 19/00 | (2006.01) | |
| A61B 8/08 | (2006.01) | |
| A61B 10/02 | (2006.01) | |
| A61B 8/00 | (2006.01) | |
| A61B 90/11 | (2016.01) | |
| A61B 17/34 | (2006.01) | |

(52) U.S. Cl.
CPC .......... *A61B 19/201* (2013.01); *A61B 8/0841* (2013.01); *A61B 8/4272* (2013.01); *A61B 10/0266* (2013.01); *A61B 90/11* (2016.02); *A61B 2017/3409* (2013.01); *A61B 2017/3413* (2013.01)

(58) Field of Classification Search
CPC ... A61B 8/0841; A61B 8/4218; A61B 8/4272; A61B 8/4483; A61B 17/3403; A61B 2017/3413; A61B 19/201
See application file for complete search history.

(56) References Cited

U.S. PATENT DOCUMENTS

| | | |
|---|---|---|
| 5,623,931 A | 4/1997 | Wung |
| 5,941,889 A | 8/1999 | Cermak |
| 6,203,499 B1 | 3/2001 | Imling |
| 6,475,152 B1 | 11/2002 | Kelly, Jr. |
| 6,485,426 B2 | 11/2002 | Sandhu |
| 7,691,066 B2 | 4/2010 | Kosaku |
| 7,846,103 B2 | 12/2010 | Cannon, Jr. |
| 7,976,469 B2 | 7/2011 | Bonde |
| 8,057,487 B2 | 11/2011 | Chu |
| 8,073,529 B2 | 12/2011 | Cermak |
| 8,118,743 B2 | 2/2012 | Park |
| 8,216,149 B2 | 7/2012 | Oonuki |
| 8,241,301 B2 | 8/2012 | Zhang |
| 8,257,264 B2 | 9/2012 | Park |

(Continued)

FOREIGN PATENT DOCUMENTS

| | | |
|---|---|---|
| CN | 201968836 U | 9/2011 |
| DE | 19808220 A1 | 9/1999 |

(Continued)

*Primary Examiner* — Matthew F Desanto

(57) ABSTRACT

The present invention presents an apparatus and methods to stereotactically guide insertion of invasive tubular devices to a tissue object of a living body. The apparatus comprises a positioning guide control assembly and a positioning guide assembly that is operably detachable from the positioning guide control assembly, and rotationally adjustable and lockable. The positioning guide control assembly releasably houses a ultrasound transducer head to visualize and target the tissue object and adjusts an insertion angle of an invasive tubular device placed in the positioning guide assembly.

7 Claims, 9 Drawing Sheets

(56) References Cited

U.S. PATENT DOCUMENTS

| | | | |
|---|---|---|---|
| 8,496,593 B2 | 7/2013 | Park | |
| 8,574,160 B2 | 11/2013 | Gorzitze | |
| 2002/0058872 A1 | 5/2002 | Steininger | |
| 2007/0073155 A1* | 3/2007 | Park | A61B 8/0833 600/461 |
| 2011/0087105 A1* | 4/2011 | Ridley | A61B 8/0833 600/459 |
| 2011/0313293 A1 | 12/2011 | Lindekugel | |
| 2012/0059260 A1 | 3/2012 | Robinson | |
| 2012/0259221 A1* | 10/2012 | Sheldon | A61B 8/462 600/439 |
| 2013/0066192 A1 | 3/2013 | Sarvestani | |
| 2013/0197355 A1 | 8/2013 | Lee | |
| 2013/0225984 A1 | 8/2013 | Cheng | |

FOREIGN PATENT DOCUMENTS

| | | |
|---|---|---|
| DE | 10015510 A1 | 4/2001 |
| SE | 524042 C2 | 6/2004 |

* cited by examiner

Figure 1
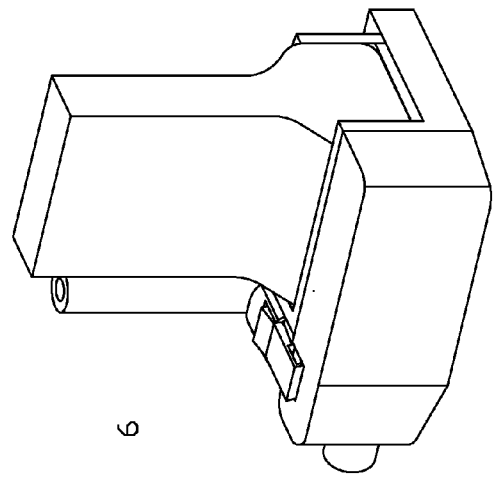
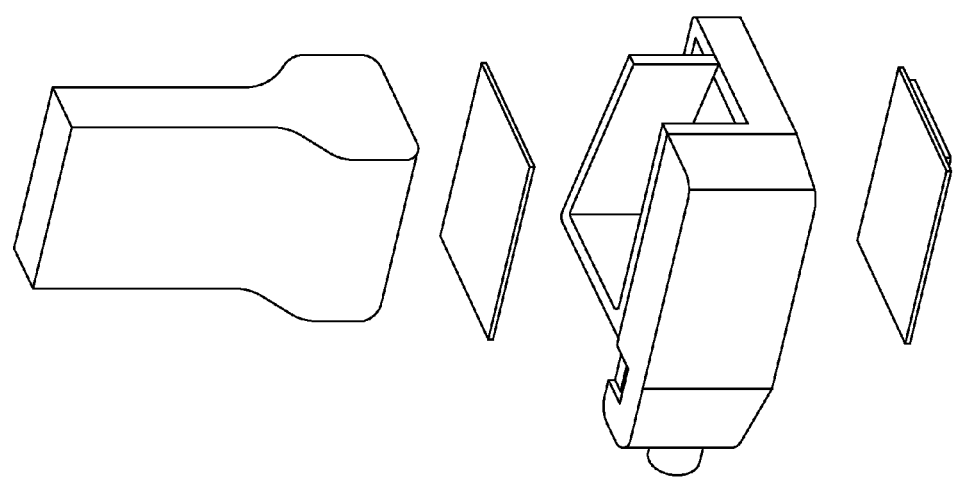
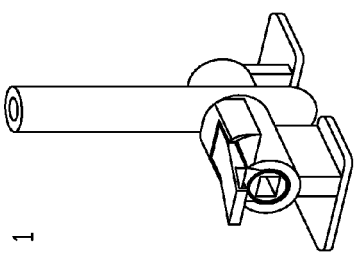

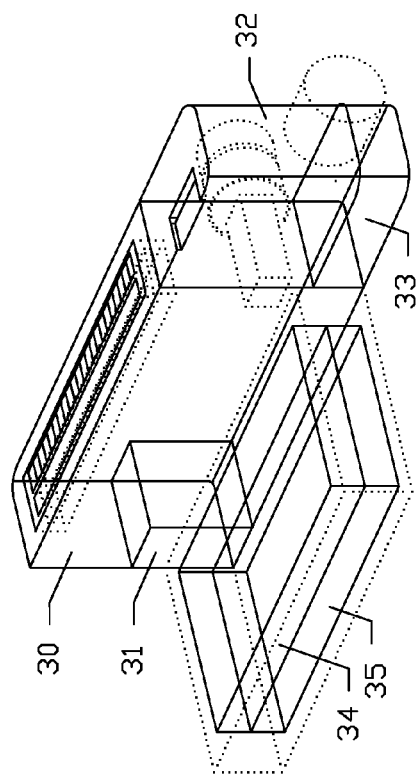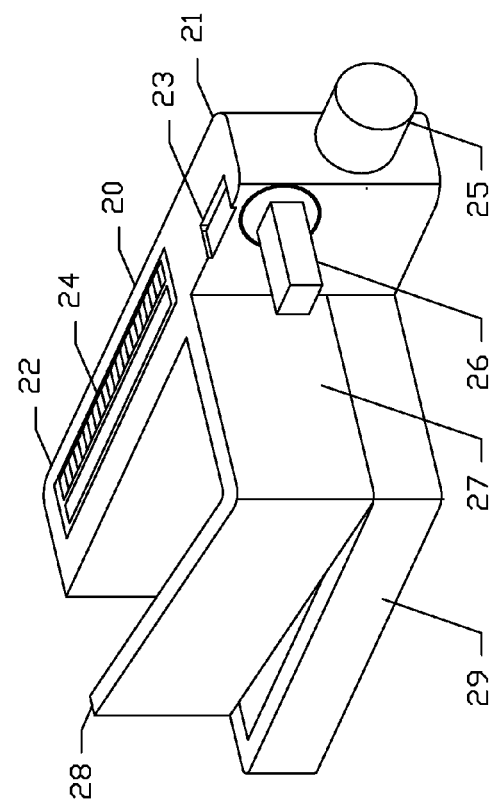
Figure 3

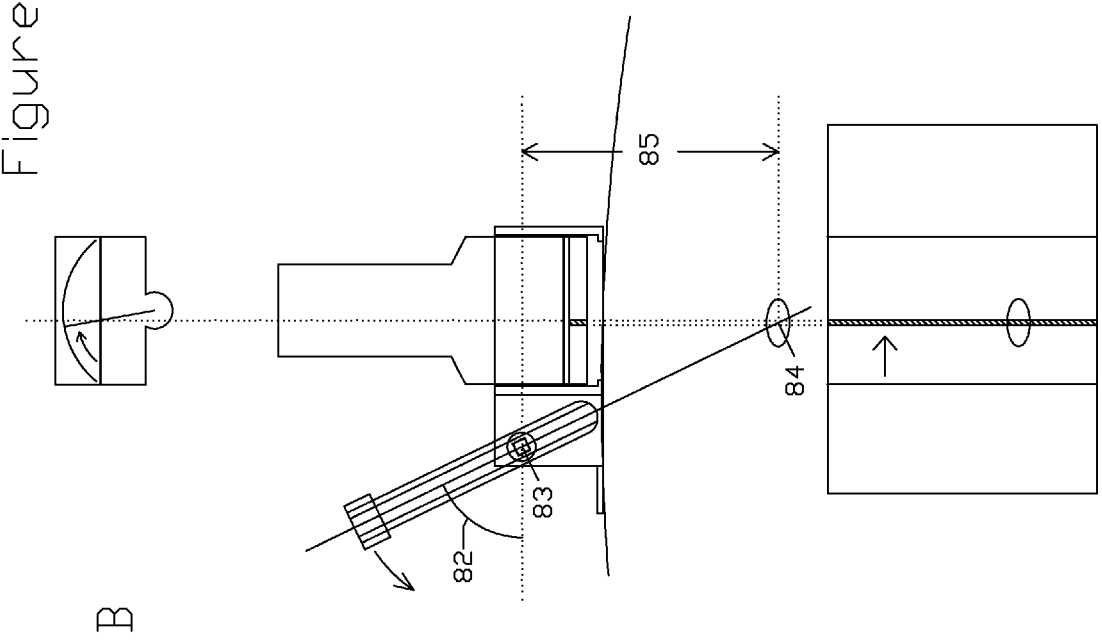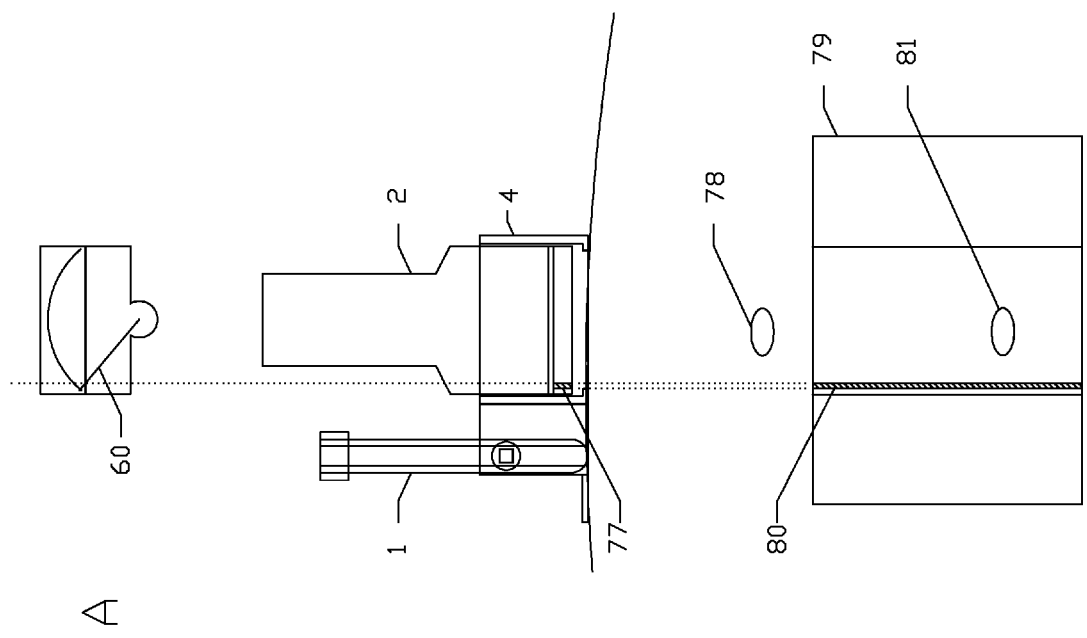
Figure 7

Figure 9
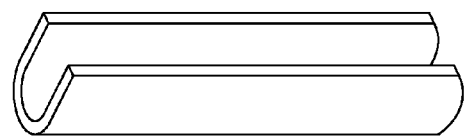
D
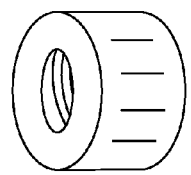 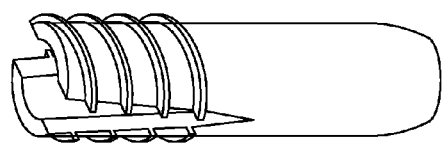
C
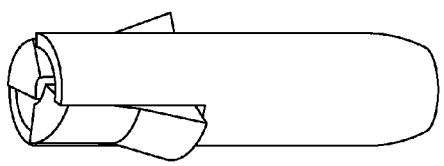
B-2
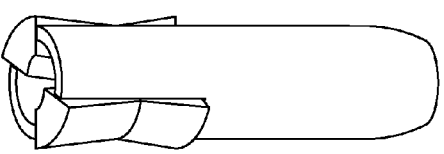
B-1
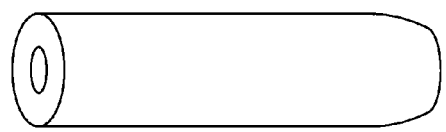
A

STEREOTACTIC POSITIONING GUIDE APPARATUS

TECHNICAL FIELD

The present invention relates generally to the field of positioning guidance of insertion of invasive devices in a living body for medical purposes. More specifically, the present invention provides an apparatus and methods to assist introduction of tubular devices into a tissue using ultrasound.

BACKGROUND OF THE INVENTION

Visual guidance using ultrasound images has been successfully used for inserting core biopsy needles into tissue to procure tissue samples from a living body, resulting in high rates of sensitivity of tissue diagnosis. Accurate positioning of a biopsy needle by ultrasound guidance can be facilitated by providing a set of numerical positioning data for the biopsy needle such as an insertion length of the needle to reach an object from a skin and an insertion angle between a longitudinal axis of the needle and a horizontal axis of an ultrasound transducer visualizing the tissue object. An insertion angle and a length of a biopsy needle to reach a tissue object could be calculated by a trigonometric measurement using a measured vertical depth from a point of a contact portion of a transducer placed on a skin to a ultrasonographically visualized tissue object and a horizontal distance from the point of the contact portion of the transducer to a rotation center of the biopsy needle.

Although assisted by ultrasonographic visualization of a tissue object, it sometimes would be technically challenging to accurately place a transducer over the tissue object and to align a point of a contact portion of the transducer substantially tangentially with a center of the tissue object. In a situation where there are a range of varying positions of a center of a small tissue object in a living body, for example, during respirations or involuntary body movements, there would be an increase in error in estimating both the insertion angle and length of the needle to reach the tissue object. These inaccuracies may be minimized if a point of a contact portion of a transducer and a center of a tissue object is ultrasonographically visualized, if the point of the contact portion of the transducer is movably adjustable in an ultrasonographic field to get linearly aligned with the center of the tissue object and if an insertion angle of a biopsy needle is rotationally adjustable at a range of ratios to positional changes of the point of the contact portion of the transducer in the ultrasonographic field in a way changes in a position of the point of the contact portion of the transducer in relation to the center of the tissue object predictably result in changes in an insertion angle of the needle toward the center of the tissue object and vice versa.

SUMMARY OF THE INVENTION

The present invention provides an apparatus that assists insertion of invasive tubular devices to tissue with ultrasonographically visualized targeting approaches to a tissue object. The invention provides a means to rotationally adjust insertion angle of invasive devices to reach the tissue object, which can be monitored in an ultrasonographic field. The invention provides a means to steady the biopsy needle at a site of needle entry to the tissue, without a need to rely on an operator's hand. The apparatus comprises a positioning guide control assembly and a positioning guide assembly that is releasably detachable from the positioning guide control assembly and operable. The positioning guide control assembly releasably houses a ultrasound transducer head, coordinates adjustment of insertion angles of invasive devices with linear alignment between a point of the transducer head and the tissue object in an ultrasonographic field.

In one embodiment, the positioning guide assembly is provided in one or a plurality of configurations, including a cross configuration which comprises an upright tubular positioning guide and a pair of transverse cylinders irreversibly attached at a right angle to each opposite side of a lower portion of the outer wall of the tubular positioning guide, respectively. One transverse cylinder serves for rotation of the tubular positioning guide and the other transverse cylinder provides the tubular positioning guide with axial stability. Each transverse cylinder is slidably and rotatably housed in a tubular cylinder holder that is attached to a base panel located below said transverse cylinder.

In one embodiment, a cylinder holder for the rotation cylinder of the tubular positioning guide has a horizontal slot for a length to accommodate a part of a lock and release lever which snaps in and out of said horizontal slot. An inner wall of the rotation cylinder holder has a plurality of substantially linear threads. In between of an outer circumferential wall of the rotation cylinder and the inner wall of the rotation cylinder holder, a thin nonslip tubular elastomer is provided, encasing the outer wall of said rotation cylinder. The horizontal slot of the rotation cylinder holder is reversibly and circumferentially expandable to a degree upon engagement with the lock and release lever, which widens an inner tubular space of said rotation cylinder holder. Widening of the inner tubular space allows friction-less rotation of both the elastomer and rotation cylinder inside said rotation cylinder holder. Disengagement of the lock and release lever shrinks the circumference of said tubular space, which then holds fast both the tubular elastomer and rotation cylinder together. The rotation cylinder is fastened by friction generated by the circumferentially squeezed tubular elastomer encasing said rotation cylinder. A transverse cylinder for axial stability slides in a tubular space of a stabilizer cylinder holder and axially stabilizes the tubular positioning guide on rotation. A mid portion of the base panel is configured to provide an open space through which an invasive device passes from the tubular positioning guide to a tissue object. An opposite side of the base panel to the cylinder attachment side is configured to provide reversible adhesion to a skin overlying the tissue object.

In one embodiment, the positioning guide assembly is configured to reversibly be fastened to the positioning guide control assembly by insertion of the lock and release lever into a slot provided on an anterior upper panel of the positioning guide control assembly and to be detached from the positioning guide control assembly by retracting said lock and release lever from said slot. Insertion of said lock and release lever into said slot is coincided with engagement of said lever with the horizontal slot of the rotation cylinder holder, which results in widening of the inner tubular space of said rotation cylinder holder. Retracting said lock and release lever from said slot of the positioning guide control assembly disengages said lever from the horizontal slot of the rotation cylinder holder, which releases the positioning guide assembly from the positioning guide control assembly and allows the rotation cylinder holder to fasten the rotation cylinder.

In one embodiment, the positioning guide control assembly is provided in one or a plurality of configurations including a modular configuration which comprises a transducer housing enclosure, a positioning controller assembly, a position alignment assembly and a power and electronic control assembly. The transducer housing enclosure is provided in an open box configuration with its top and bottom portions open to allow a proximal portion of the transducer to slip in and out of said enclosure through the top portion and to allow a face portion of the transducer to contact an upper part of the position alignment assembly via a solid gel panel. The transducer housing enclosure is configured to hold fast the proximal portion of the transducer in a manner to align longitudinal and horizontal axes of the transducer in parallel with longitudinal and horizontal axes of said transducer housing enclosure, respectively. The horizontal axis of the transducer is used as a reference axis for the rotatable knob to calibrate angular displacement of the tubular positioning guide and the longitudinal axis of the transducer is used as a reference axis for the rotation cylinder to align a longitudinal axis of the tubular positioning guide with said longitudinal axis of the transducer.

In one embodiment, the positioning controller assembly is provided in one or a plurality of configurations including a rectangular box configuration which encloses a worm drive arrangement, a part of an electromagnetic pointing device of the position alignment assembly and the power and electronic control assembly. The worm drive comprises a longitudinal worm connected at a right angle to a worm gear with an output shaft of the worm gear protruding through a medial vertical sidewall of said rectangular box. A proximal end of the worm shaft is connected to a rotatable knob located outside an anterior sidewall. The output shaft of the worm gear is provided in one or a plurality of configurations including a longitudinal bar having more than two internal angles on cross-section of said bar. The output shaft releasably is inserted in a horizontal slot of the rotation cylinder of the tubular positioning guide of the positioning guide assembly. The rotation cylinder is rotated by the output shaft of the worm gear by rotation of the rotatable knob that transmits worm rotation to the worm gear.

In one embodiment, an angle encoder is coaxially connected to the worm shaft, which measures rotational displacement of the worm. The angle encoder is electronically connected to the power and electronic control assembly that relays an electronic information from said angle encoder of rotational displacements of the worm shaft to the electromagnetic pointing device of the position alignment assembly.

In one embodiment, the position alignment assembly is provided in one or a plurality of electromechanical configurations, which comprises a substantially ultrasound-transparent flat rectangular box and the electromagnetic pointing device adjoining a central portion of one lateral sidewall of said flat rectangular box. The flat rectangular box is located below the face of the transducer, is filled with an ultrasound-transparent liquid. In one example, the electromagnetic pointing device comprises an electromagnetic motor to which a linear movable pointer is perpendicularly attached. The linear movable pointer is configured to protrude into a space in the flat rectangular box, to move inside said flat rectangular box from side to side and to block ultrasound transmission, which is visualized in a ultrasonographic view. A leakproof housing for the electromagnetic motor merges and seals off the flat rectangular box in one piece. An electromagnetic motor configuration comprises a U-shaped set of electromagnetic windings surrounding a central rotor. At the junction between the electromagnetic motor and the lateral sidewall of the flat rectangular box, there is provided an open conduit in said lateral sidewall. An open end of the U shape of the windings is connected to both sides of the open conduit through which a part of the rotor protrudes into the space of the flat rectangular box. The outer surface of the rotor is helically threaded and is configured to drive a longitudinal worm which in turn linearly moves the linear movable pointer via a rack and pinion movement. In another example, the electromagnetic pointing device comprises a galvanometer-type device that uses varying electric current or electric resistance to radially move the linear movable pointer around a center of said device. Similar to the configuration for the electromagnetic motor, the galvanometer-type device is sealed off together with the flat rectangular box in one piece.

In one embodiment, the power and electronic control assembly is provided in one or a plurality of configurations including a rectangular box configuration which has a segment digital display on a top portion. An integrated circuit board is located under and electronically connected to the segment digital display. A compartment for replaceable batteries is located below the integrated circuit board and connects batteries electrically with the integrated circuit board, the segment digital display, the angle encoder and the electromagnetic pointing device. The power and electronic control assembly is located in an upper part of the positioning controller assembly and the segment digital display is configured to be visible through an upper panel of the positioning controller assembly. The segment digital display shows at least a set of digitized numerical information about angular displacement of the rotation cylinder of the positioning guide assembly connected to the worm gear and distance from a position of the linear movable pointer tangentially placed over the tissue object to said tissue object.

In another embodiment, the power and electronic control assembly is configured to control movements of the electromagnetic pointing devices upon an electronic input from the angle encoder. In this configuration, rotations of the rotation cylinder of the positioning guide assembly by the rotatable knob of the worm drive arrangement translate into ultrasonographically visualizable movements of the linear movable pointer in parallel to the transducer face located above the flat rectangular box of the position alignment assembly. In a two-dimensional ultrasonographic view, the linear movable pointer is configured to produce a thin vertical blank shadow line that can be distinguished readily from surrounding tissue images. Rotations of said rotation cylinder are configured to match horizontal movements of said linear movable pointer in ways that a longitudinal axis of an invasive device at an insertion angle in the positioning guide assembly crosses a vertical blank shadow line at a center of a tissue object in the two-dimensional ultrasonographic view.

In one embodiment, a distance (a) from a proximal portion of the transducer to a center of a tissue object is calculated by a substantially tangential placement of the proximal portion of the transducer to a skin overlying the tissue object. A horizontal distance from a rotation center of the rotation cylinder of the positioning guide assembly to a vertical line on a linear movable pointer measures as (b). Using a simple trigonometry, a distance (h) of an invasive device from the rotation center of the rotation cylinder to the center of the object equals a square root of $(a^2+b^2)$ and a sine of an angle (a) of the rotation cylinder is calculated as a ratio of (a) to (h). The horizontal distance (b) is variable based on a moving position of the linear movable pointer.

In one embodiment, following placement of a transducer housed in the positioning guide apparatus of the present invention on a skin overlying a tissue object, the rotatable knob is configured to put numerical information of a measured distance (a) from the center of the tissue object vertically up to a point horizontal to the rotation center of the rotation cylinder into an electronic control circuit, to rotate the rotation cylinder of the positioning guide assembly to a certain angle (cc) in relation to the horizontal axis of the proximal portion of the transducer head and to get locked in to prevent an unintended rotation of said rotatable knob. The segment digital display shows at least two lines of numerical information, i.e., distance (a) and angle (a). Input function of the rotatable knob is changeable by a plurality of pulled-out positions of the rotatable knob along the worm shaft of the worm drive arrangement. The rotatable knob is pulled out to an outermost position to get disengaged from the worm shaft to put in numerical information of a distance (a). A first inward position of the rotatable knob from the outermost position allows said rotatable knob to get engaged with the worm shaft to rotate the worm that moves the linear movable pointer located below the proximal portion of the transducer horizontally to a point directly vertical to the center of the tissue object underneath in an ultrasonographic view. The rotatable knob of said worm drive arrangement simultaneously rotates the rotation cylinder of the tubular positioning guide of the positioning guide assembly at a ratio to the movement of said linear movable pointer until a longitudinal axis of an invasive device placed in the tubular positioning guide crosses at a sine of an angle ($\alpha$) of said tubular positioning guide a vertical shadow line between the linear movable pointer and the tissue object at a center of said tissue object. A second inward position of the rotatable knob locks in said knob to prevent further rotations.

In one embodiment, the tubular positioning guide is provided in one or a plurality of configurations for a range of function of said tubular positioning guide. For conventional needle biopsy procedures, the tubular positioning guide is provided in a range of fixed tubular gauges to accommodate a range of needle sizes. For inserting vascular devices and their accessories, the tubular positioning guide is provided as semicircular tubular, which is to allow open access and insertion of more than one device during one session of a procedure and unobstructed interchangeable removal of devices. For therapeutic procedures such as insertion of a probe for radiofrequency ablation of a lesion, for an example, the tubular positioning guide is provided with devices to fasten such probes for an extended period of time.

BRIEF DESCRIPTION OF THE DRAWINGS

FIG. 1 shows a schematic illustration of an example of individual components of the apparatus of the present invention. FIG. 1-1 represents an example of a positioning guide assembly; 2 represents an ultrasound transducer head; 3 represents a solid gel panel; 4 represents a positioning guide control assembly; 5 represents a second solid gel panel; 6 represents a fully assembled apparatus with an ultrasound transducer in place.

FIG. 2A represents a positioning guide assembly with a lock and release lever engaged with a rotation cylinder holder; FIG. 2B represents a positioning guide assembly with a disengaged lock and release lever; FIG. 2C shows a fully-deployed positioning guide assembly with a disengaged lock and release lever and a rotated tubular positioning guide.

FIG. 3 shows a schematic example of the positioning guide control assembly: FIG. 3A represents an external view; FIG. 3B shows individual compartments inside the positioning guide control assembly with a transducer housing removed for illustration.

FIG. 4A shows a fully assembled view of the positioning guide assembly; FIG. 4B shows individual components in detail.

FIG. 5A shows a three-quarter view of a fully assembled components; FIG. 5B highlights a worm drive arrangement; FIG. 5C shows a position alignment assembly; FIG. 5D shows individual components of a galvanometer-type position alignment assembly.

FIG. 6A shows a galvanometer-type position alignment assembly and its method of movement; FIG. 6B shows a position alignment assembly based on an electromagnetic motor and its method of movement; FIG. 6C shows individual components of the electromagnetic-motor-based position alignment assembly.

FIGS. 7A & 7B depict a schematic illustration of an example of a method of coordination of an angular rotation of the tubular positioning guide with a linear movement of a linear movable pointer of the position alignment assembly to aim at a center of a tissue object.

FIG. 9 illustrates schematic examples of various configurations of the tubular positioning guide.

DETAILED DESCRIPTION OF THE DRAWINGS

Figure 2:
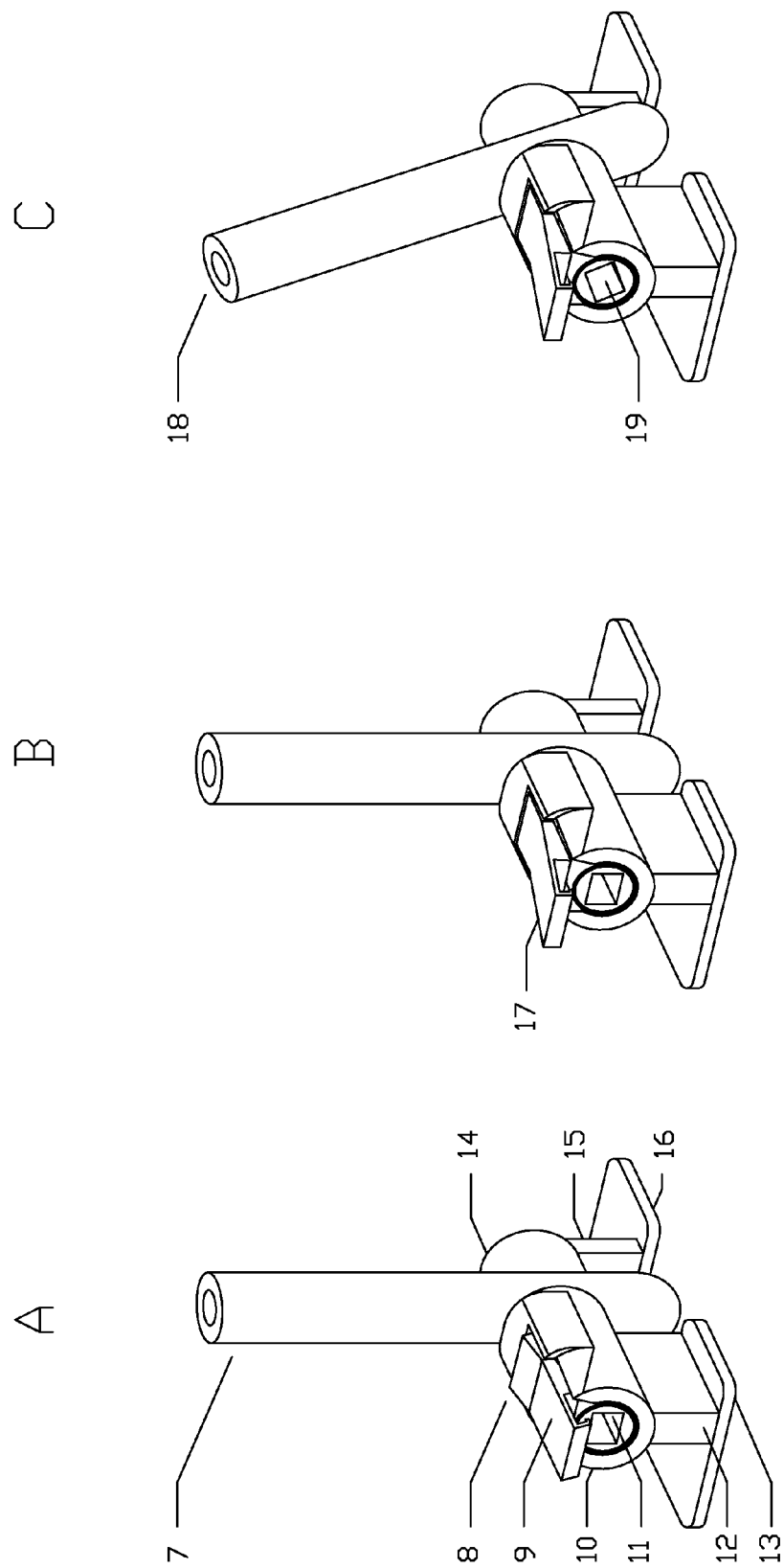
FIG. 2 shows a schematic example of the positioning guide assembly of the apparatus.

As described below, the present invention provides a positioning guide apparatus visually and stereotactically targeting a tissue object and methods of use. It is to be understood that the descriptions are solely for the purposes of illustrating the present invention, and should not be understood in any way as restrictive or limited. Embodiments of the present invention are preferably depicted with reference to FIGS. 1 to 9, however, such reference is not intended to limit the present invention in any manner. The drawings do not represent actual dimension of devices, but illustrate the principles of the present invention.

FIG. 1 shows a schematic example of individual components of the apparatus of the present invention. An example of a positioning guide assembly is shown in 1, which can be reversibly fastened to and detached from a positioning guide control assembly 4. An ultrasound transducer head 2 slides in and gets reversibly fastened to the positioning guide control assembly 4 and visualizes a tissue below through a couple of solid gel panels 3 and 5. An upper surface of the solid gel panel 3 placed in an open space provided in the positioning guide control assembly directly contacts a face of the ultrasound transducer head above and a lower surface of the other gel panel 5 placed in a most distal space of the said positioning guide control assembly contacts a skin below overlying the tissue. A lower surface of the solid gel panel 3 and an upper surface of the solid gel panel 5 contact a part of the positioning guide control assembly located in between of said solid gel panels 3 and 5. Solid gel panels improve transmission of ultrasound waves between the tissue and the ultrasound transducer. An example of a fully assembled apparatus is shown in 6. The positioning guide assembly 4 and the solid gel panels 3 and 5 are non-reusable.

FIG. 2 shows a schematic example of the positioning guide assembly of the apparatus: FIG. 2A represents a positioning guide assembly in a fastened configuration to the positioning guide control assembly. In this particular configuration, the positioning guide assembly comprises a tubular positioning guide 7 in an upright position, a positioning guide anchoring and rotation assembly 8 and a stabilizer cylinder holder 14. The positioning guide anchoring and rotation assembly 8 comprises a lock and release lever 9 reversibly inserted in a rotation cylinder holder 10 and a rotation cylinder 11 encircled by said rotation cylinder holder 10. Both the rotation and stabilizer cylinder holders 10 and 14 are not attached to the tubular positioning guide 7 but irreversibly attached to an upper surface of a pair of bottom plates. The rotation cylinder holder 10 is connected to a bottom plate 13 via an attachment bar 12. The stabilizer cylinder holder 14 is connected to a bottom plate 16 via an attachment bar 15. FIG. 2B represents a configuration of the positioning guide assembly with the lock and release lever 17 disengaged from the rotation cylinder holder. FIG. 2C shows a fully-deployed positioning guide assembly following detachment from the positioning guide control assembly. A tubular positioning guide 18 is rotated around a longitudinal axis 19 of the rotation cylinder and fixed at an angle. A lower surface of both the bottom plates 13 and 16 has a means such as an adhesive to reversibly adhere to a skin.

FIG. 3 shows a schematic illustration of an example of the positioning guide control assembly. FIG. 3A represents an external three-quarter view which shows a positioning controller assembly 20 having a proximal end 21 and a distal end 22, a transducer housing enclosure 27 having a flexible free wall 28 and a position alignment assembly housing 29. The free wall 28 is flexible at a joint with an anterior sidewall of the transducer housing enclosure 27 in a manner that a transducer head is held fast inside the transducer housing enclosure 27. On an anterior upper surface of the positioning controller assembly 20, a slot 23 is provided vertically above an output shaft 26 of a worm drive arrangement, which fastens the lock and release lever 9 of the positioning guide assembly depicted in FIG. 2A to said positioning guide control assembly. The output shaft 26 releasably is inserted in a slot of the rotation cylinder 11 of FIG. 2A and rotates said rotation cylinder 11 as shown in FIG. 2. A segment digital display 24 of a power and electronic control assembly is visible on the upper surface of said positioning controller assembly 20 along a longitudinal border. A rotatable knob 25 is connected to the worm drive arrangement inside said positioning controller assembly 20 through an anterior sidewall. FIG. 3B shows individual compartments inside the positioning guide control assembly with a transducer housing enclosure removed for illustration. The positioning controller assembly 20 has a longitudinally rectangular compartment 30 which anteriorly adjoins a worm drive arrangement compartment 32 and a compartment 33 of a part of an electronic control assembly. The compartment 30 houses the power and electronic control assembly including a battery compartment 31, a part of the worm drive arrangement and a part of the positioning alignment assembly. A main part of the position alignment assembly is enclosed in a compartment 34 below which a compartment 35 releasably holds a solid gel panel. A lateral sidewall of both the compartments 34 and 35 adjoins a medial sidewall of the positioning controller assembly compartment 30 at a right angle.

Figure 4:
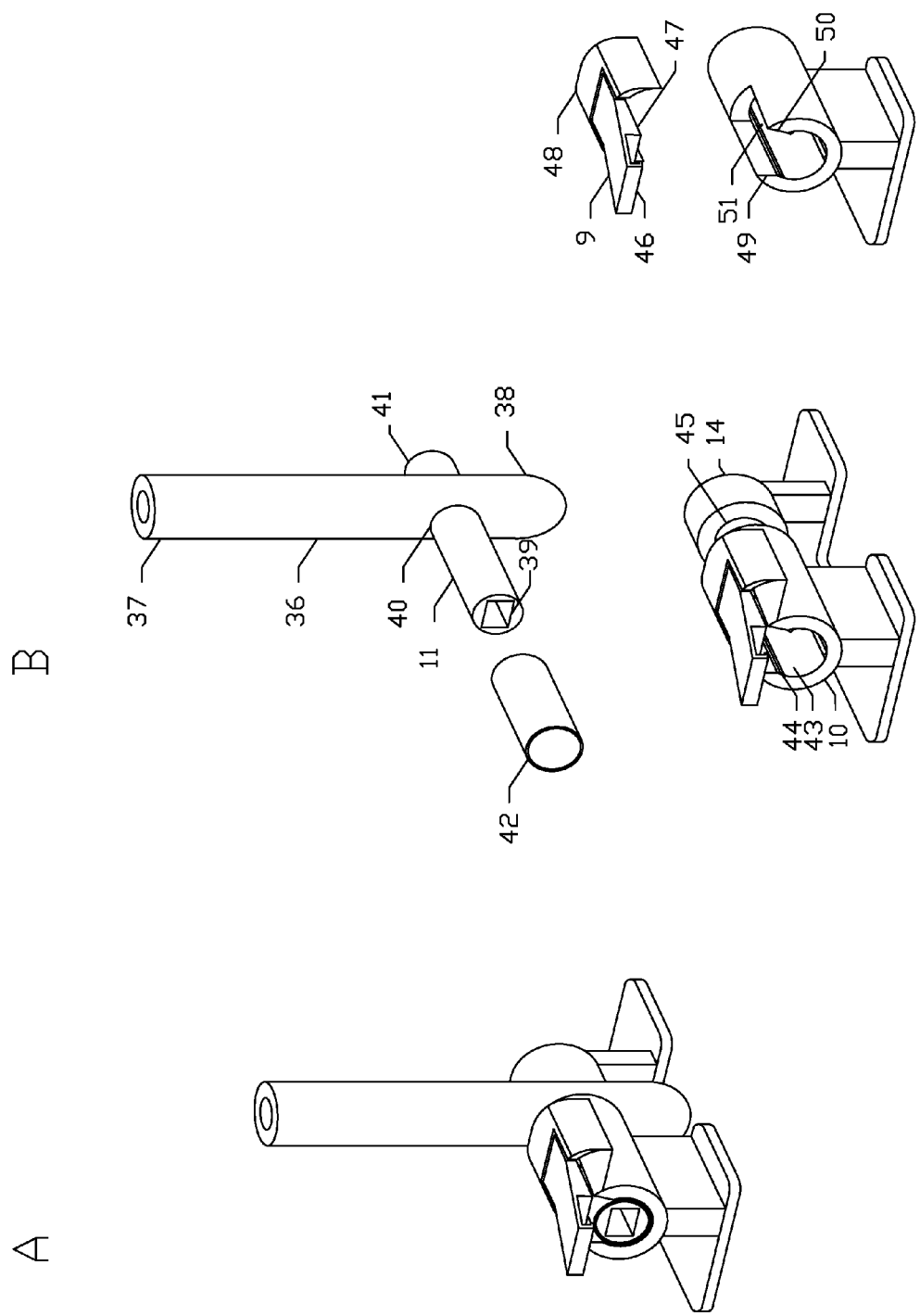
FIG. 4 shows a schematic example of individual components of the positioning guide assembly.

FIG. 4 shows a schematic illustration of an example of individual parts of the positioning guide assembly. FIG. 4A shows a fully assembled view of the positioning guide assembly. FIG. 4B shows the tubular positioning guide 36 having a top portion 37 for entry of an invasive device and a tip 38 through which the invasive device protrudes. The tubular positioning guide 36 is irreversibly attached in a cross configuration to a medial end 40 of the rotation cylinder 11 and to a stabilizer cylinder 41 in a similar manner. The stabilizer cylinder 41 slidably is inserted in an inner tubular space 45 of the stabilizer cylinder holder 14. Inside the rotation cylinder 11, a longitudinal slot 39 is provided to reversibly accommodate the output shaft 26 of FIG. 3A. The rotation cylinder 11 is encased by a thin nonslip tubular elastomer 42 which is located in between of an outer wall of the rotation cylinder 11 and an inner wall 43 of the rotation cylinder holder 10 and which provides friction on both the walls. A plurality of horizontally linear threads 44 are irreversibly attached to the inner wall 43, which is configured to provide firm grasp of the rotation cylinder 11. The rotation cylinder holder 10 has an upper part of a tubular wall cut out to form a horizontal slot 51 bordered by a pair of cut surfaces 49 and 50 of the tubular wall. The lock and release lever 9 is configured as rocker switch which is housed in a dome enclosure 48 fixedly sitting atop the rotation cylinder holder 10 and has a proximal anchor 46 and an insertable block 47. The proximal anchor 46 reversibly is anchorable to the slot 23 of FIG. 3A. Once a proximal part of the lock and release lever 9 is pressed down, the insertable block 47 reversibly engages with the horizontal slot 51 to widen a circumference of the rotation cylinder holder 10.

Figure 5:
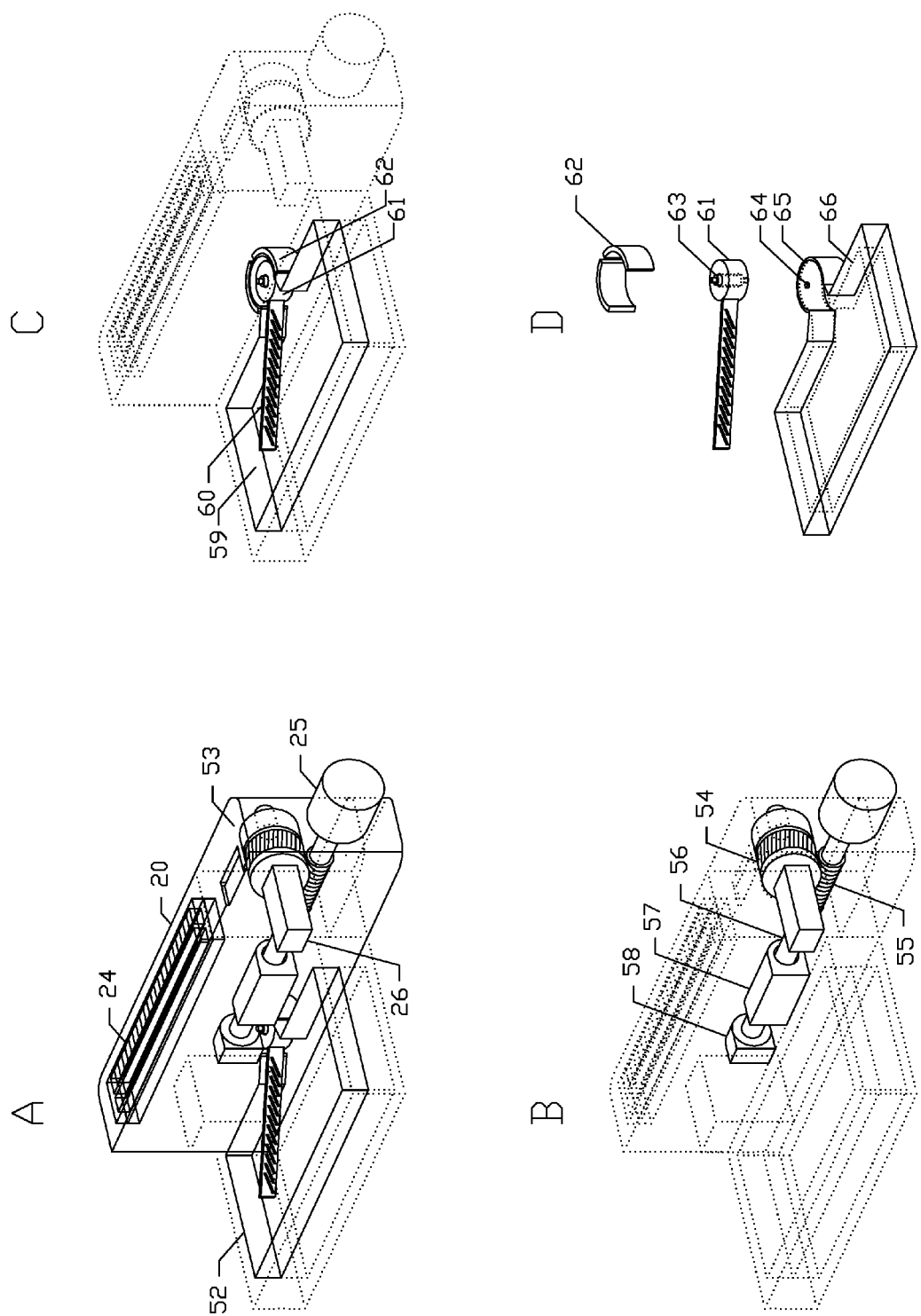
FIG. 5 shows a schematic example of individual components of the positioning guide control assembly.

FIG. 5 shows a schematic illustration of an example of individual components of the positioning guide control assembly. FIG. 5A shows a fully assembled components having the segment digital display 24 of the power and electronic control assembly on top of the positioning guide controller assembly 20, the worm drive arrangement 53 connected to the output shaft 26 and the rotatable knob 25 and the position alignment assembly 52 adjoining at a right angle the positioning controller assembly 20 and below the transducer housing enclosure that is removed in this view for a purpose of illustration. FIG. 5B shows components of the worm drive arrangement which comprises a worm gear 54 rotatably connected at a right angle to a worm 55, a worm shaft 56, a shaft anchoring portion 57 and an angle encoder 58. In FIGS. 5A and B, the rotatable knob 25 rotates the worm 55 which in turn rotates the worm gear 54. Rotations of the worm 55 are sensed by the angle encoder 58 for rotational displacements and the output shaft 26 transmits rotations of the worm gear 54 to the rotation cylinder 11 of FIG. 2. The shaft anchoring portion 57 is fixedly attached to an inner lateral sidewall of the positioning guide controller assembly 20 and supports the worm shaft 56. FIG. 5C shows a galvanometer-type position alignment assembly which comprises a flat rectangular box space 59, an electromagnetic pointing device comprising a linear movable pointer 60 attached to a pivoting wire core 61 and a set of surrounding electromagnetic windings 62. The flat rectangular box is made of substantially ultrasound-transparent polymer(s), filled with one or a plurality of type(s) of substantially ultrasound-transparent liquid and leakproof. The linear movable pointer 60 is configured to have a means to reduce drag upon moving inside the liquid. In this particular example, the pointer is fenestrated to reduce an overall lateral surface area of the pointer. FIG. 5D shows one example of a configuration of individual components of an electromagnetic pointing device of the galvanometer-type position alignment assembly, comprising a pivoting wire core 61 with an electrode connection center hub 63 and a pair of electromagnetic windings 62. The pivoting wire core 61 is enclosed by a circular outer housing 65 which adjoins an outer wall 66 of the flat rectangular box. The circular outer housing 65 has an electrode connection hub 64 which comes in contact with the electrode connection center hub 63 of the pivoting wire core 61. The windings 62 are located outside the circular outer housing 65 and encircles tightly said outer housing. Both the pivoting wire core and the windings are electrically connected to the power and electronic control assembly.

Figure 6:
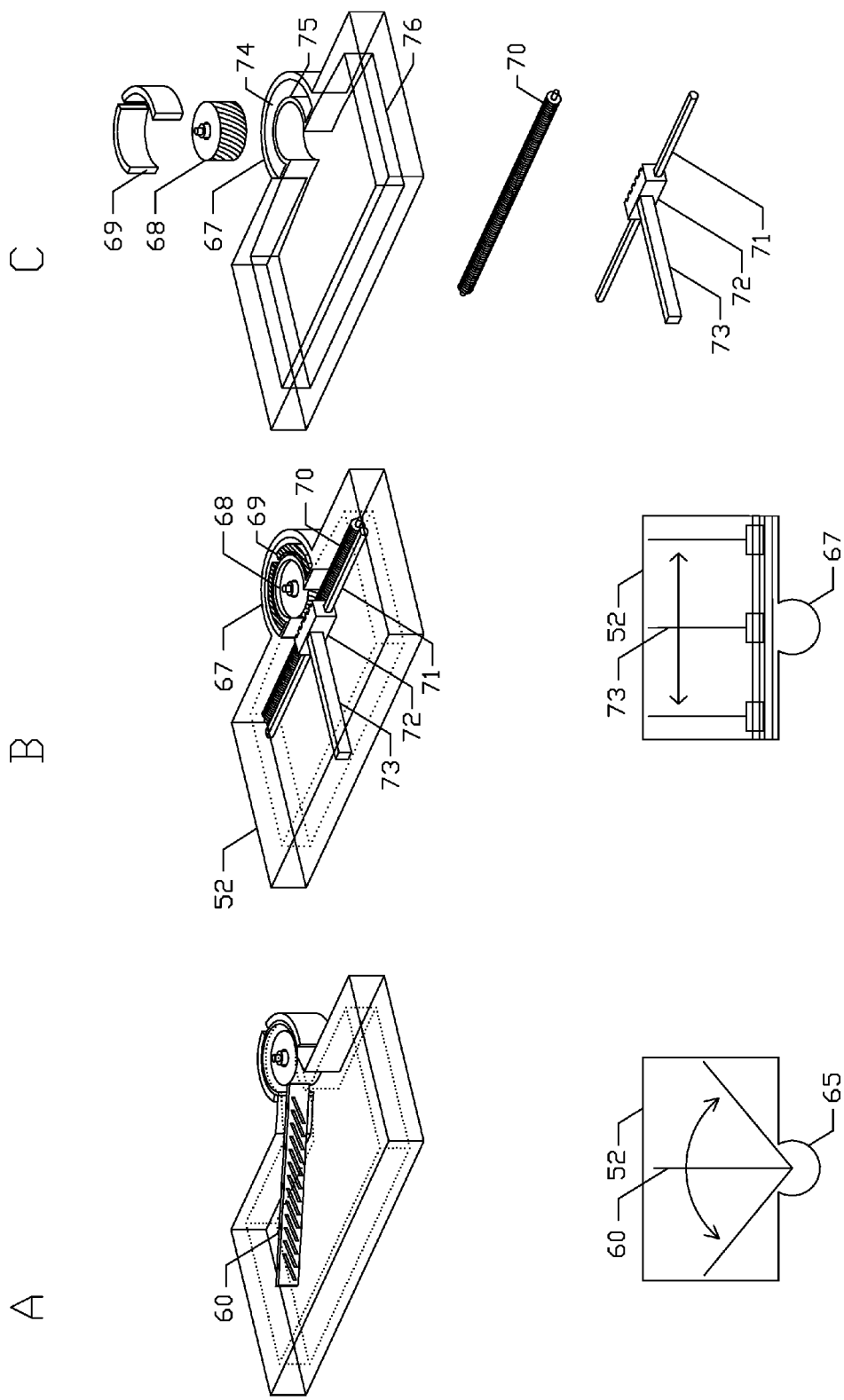
FIG. 6 shows a schematic illustration of examples of a position alignment assembly.
Figure 8:
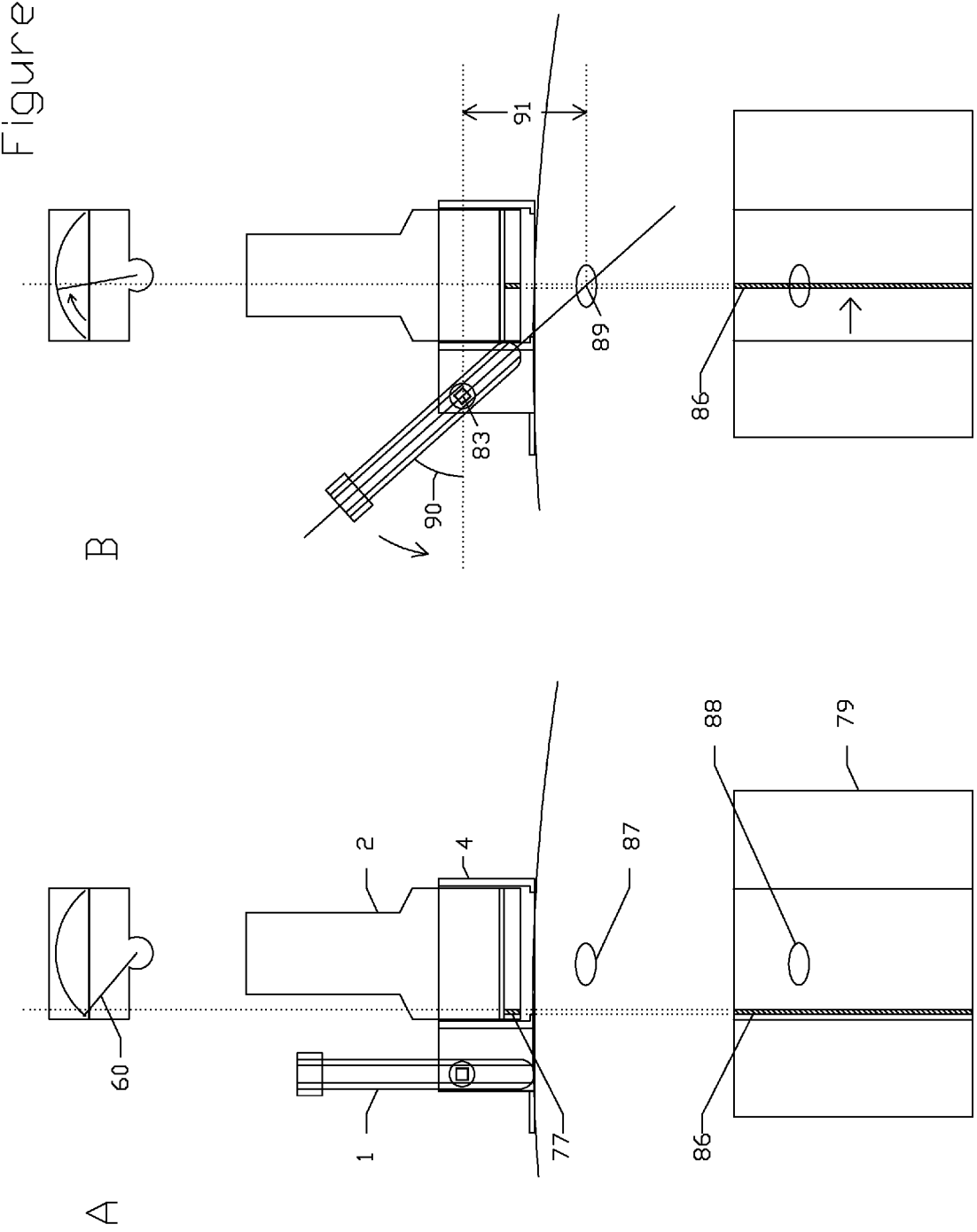
FIGS. 8A and 8B show another example of a method of coordination of an angular rotation of the tubular positioning guide with a linear movement of a linear movable pointer of the position alignment assembly to aim at a center of a tissue object that is closer to the ultrasound transducer, demonstrating a change in an insertion angle of the tubular positioning guide based on a vertical distance.

FIG. 6 shows a schematic illustration of examples of a position alignment assembly. In FIG. 6A, a linear movable pointer 60 is configured to move radially about a pivoting wire core upon changes in electric current or resistance, similar to movements of a pointer of a typical galvanometer upon changing electric currents. Changes in electric current or resistance are controlled and provided by the power and electronic control assembly. FIG. 6B shows a position alignment assembly based on a configuration of an electromagnetic motor, comprising a circular outer housing 67, a set of electromagnetic windings 69, a helically threaded pivoting rotor 68 connected in a sufficient lead angle for rotation to a corresponding worm gear 70, a movable rack 72 sliding over a rack rod 71 from side to side and a linear movable pointer 73 attached to said movable rack at a right angle. In this configuration, the linear movable pointer moves horizontally from one end to the other end of the flat rectangular box. Compared to a radial movement of a linear movable pointer, a horizontal movement of a linear movable pointer produces a thinner area of blocked ultrasound transmissions in a two dimensional ultrasonographic view. FIG. 6C shows an exploded view of an example of the electromagnetic-motor-based device. The electromagnetic windings 69 are enclosed in a semicircular space 74 which adjoins an outer wall of the flat rectangular box 52. The helically threaded pivoting rotor 68 is enclosed by an inner semicircular wall 75 which adjoins an inner wall 67 of said flat rectangular box. The entire components of the configuration are housed in a leakproof and substantially ultrasound-transparent enclosure and an inner space of the flat rectangular box is similarly filled with one or a plurality of substantially ultrasound-transparent liquid(s).

FIGS. 7A & 7B depict a schematic illustration of an example of a method of guidance of a tubular positioning guide by the present invention. In both 7A and 7B, upper drawings represent a schematic top-down view of a position alignment assembly showing a linear movable pointer 60 radially moving. Mid drawings show a schematic profile view of the apparatus placed atop a skin overlying a tissue object 78. Lower drawings depict a schematic ultrasonographic two-dimensional view 79 seen in a monitor of a ultrasonographic machine. As illustrated in FIG. 7A, once the apparatus is placed on the skin above the tissue object 78, a linear movable pointer 77 generates a linear blank shadow line 80 in the two-dimensional view 79 by blocking off an ultrasonographic transmission. In this particular illustration, the linear blank shadow 80 is seen separated in a distance from an ultrasonographic image 81 of the tissue object 78. A rotation of the rotation cylinder of the positioning guide assembly about a rotation center 83 calculates an angle 82 based on a vertical distance 85, which electronically translates into a corresponding horizontal movement of the linear movable pointer to a center 84 of the tissue object, which is monitored real-time in the two-dimensional ultrasonographic view. The linear blank shadow line crossing the center of the tissue object visually confirms a linear alignment between the linear movable pointer and the center of the tissue object. The present invention is configured to match angulation of the positioning guide assembly with horizontal movement of the linear movable pointer in ways to have a longitudinal axis of the positioning guide assembly cross the linear blank shadow line at the center of the tissue object.

FIGS. 8A & 8B show another example of a method of guidance of a tubular positioning guide for a tissue object 87 that is located closer to the ultrasound transducer than depicted in FIGS. 7A and 7B, illustrating an effect of a vertical distance on an insertion angle. In FIG. 8A, a linear movable pointer 77 generates a linear blank shadow line 86 in the two-dimensional view 79 by similarly blocking off an ultrasonographic transmission. An ultrasonographic image 88 of the tissue object 87 is visualized in an upper area of the two-dimensional view than in FIG. 7A. As shown in FIG. 8B, a more acute angle 90 is calculated from a shorter vertical distance 91 between the center 89 of the tissue object and a horizontal line from the rotation center 83 while the vertical blank shadow line 86 moves the same distance as in FIG. 7B.

FIG. 9 illustrates schematic examples of various configurations of the tubular positioning guide of the apparatus of the present invention. For conventional needle biopsy procedures, FIG. 9A shows a configuration for a range of fixed gauges of an inner tubular space to accommodate a range of sizes of invasive devices. FIGS. 9B and 9C show configurations of a tubular body to fasten needles and probes for diagnostic and therapeutic purpose which requires a steady maintenance of a position of an invasive device for a duration of the procedure. One example uses a pair of depressible knobs located longitudinally in a tubular wall, as shown in FIG. 9-B 1. An internal lumen of the tubular guide is narrowed by pushing the pair of the depressible knobs, which holds fast an invasive device inside the internal lumen. Another example uses a cap with internal threads which rotatably narrow an internal lumen of a threaded tubular guide and fasten an invasive device inside said tubular guide. FIG. 9D shows a configuration of a semicircular tube which allows an open access to said tubular guide and insertion of more than one device during one session of a procedure and unobstructed interchangeable removal of devices.

It is to be understood that the aforementioned description of the apparatus and methods is simple illustrative embodiments of the principles of the present invention. Various modifications and variations of the description of the present invention are expected to occur to those skilled in the art without departing from the spirit and scope of the present invention. Therefore the present invention is to be defined not by the aforementioned description but instead by the spirit and scope of the following claims.

What is claimed is:
1. A stereotactic positioning guide apparatus, comprising:
a positioning guide assembly, and a positioning guide control assembly;
the positioning guide assembly, wherein the positioning guide assembly comprises a tubular positioning guide, a rotation cylinder assembly, and a lock and release lever configured to couple with and to uncouple from the positioning guide control assembly, wherein the rotation cylinder assembly comprises a rotation cylinder, wherein the lock and release lever of the positioning guide assembly is configured to synchronize coupling the positioning guide assembly with the positioning guide control assembly for operational control of the positioning guide assembly by the positioning guide control assembly with letting the rotation cylinder be rotatable, wherein the positioning guide assembly is configured to synchronize uncoupling the positioning guide assembly from the positioning guide control assembly with locking the rotation cylinder so as to guide an invasive tubular device inside the tubular positioning guide slidably passing therethrough, wherein the positioning guide assembly is configured to be independently operable for the guiding of the invasive tubular device inside the tubular positioning guide following the uncoupling from the positioning guide control assembly, wherein the positioning guide assembly is configured to rotationally adjust and reversibly lock the tubular positioning guide for insertion angle of the invasive tubular device; and the positioning guide control assembly, wherein the positioning guide control assembly comprises an electromagnetic pointing device, a positioning controller assembly, a power and electronic control assembly, and an ultrasound transducer enclosure, wherein the positioning controller assembly comprises a manually-drivable worm drive arrangement, wherein the positioning guide control assembly is configured to visually locate a tissue object by the electromagnetic pointing device in a visualized ultrasonographic field so as to align a longitudinal axis of the tubular positioning guide of the positioning guide assembly with the tissue object in the visualized ultrasonographic field, and wherein the positioning guide control assembly is configured to synchronize locating the tissue object by the electromagnetic pointing device with aligning the longitudinal axis of the tubular positioning guide of the positioning guide assembly with the tissue object by manually rotating the manually-drivable worm drive arrangement.

2. The stereotactic positioning guide apparatus according to claim 1, wherein the positioning guide control assembly further comprises:

the power and electronic control assembly, wherein the power and electronic control assembly comprises an integrated circuit board and a battery, wherein the power and electronic control assembly is configured to electronically synchronize locating the tissue object by the electromagnetic pointing device with aligning the longitudinal axis of the tubular positioning guide of the positioning guide assembly with the tissue object;

a positioning controller assembly, wherein the positioning controller assembly comprises an angle encoder coaxially connected to a worm shaft of the manually-drivable worm drive arrangement, wherein the worm shaft of the manually-drivable worm drive arrangement is configured to be manually rotatable, wherein the angle encoder is configured to electronically measure rotational displacement of the worm shaft, wherein the worm shaft is configured to transmit rotation of the worm shaft through a worm gear of the manually-drivable worm drive arrangement to the rotation cylinder of the positioning guide assembly, and wherein the angle encoder is configured to be electronically connected to the electromagnetic pointing device and to the power and electronic control assembly; and the electromagnetic pointing device, wherein the electromagnetic pointing device comprises an electromagnetic motor and a linear movable pointer, wherein the linear movable pointer is configured to mate with the electromagnetic motor in a rack and pinion configuration, wherein the linear movable pointer is driven by the electromagnetic motor from a first sidewall to a second sidewall of an electromagnetic pointing device enclosure in parallel with a transverse axis of the electromagnetic pointing device enclosure, wherein the electromagnetic pointing device is configured to be located in front of and in parallel with a face of an ultrasound transducer slidably housed in the ultrasound transducer enclosure, wherein the electromagnetic pointing device is configured to be powered and controlled by the power and electronic control assembly, wherein the electromagnetic pointing device is configured to be electronically synchronized with the positioning controller assembly by the power and electronic control assembly, wherein the linear movable pointer of the electromagnetic pointing device is configured to produce a linear shadow line in the visualized ultrasonographic field by blocking transmission of a portion of ultrasonographic waves from the ultrasound transducer passing through the electromagnetic pointing device to the tissue object, and wherein the electromagnetic pointing device is configured to synchronize movement of the linear movable pointer with rotatably aligning the longitudinal axis of the tubular positioning guide of the positioning guide assembly with the tissue object by manually rotating the worm shaft of the manually-drivable worm drive arrangement of the positioning controller assembly.

3. The electromagnetic pointing device according to claim 2, wherein the electromagnetic pointing device is configured to transmit the ultrasonographic waves from the ultrasound transducer through the electromagnetic pointing device to the tissue object except that the linear movable pointer of the electromagnetic pointing device is configured to block transmission of the ultrasonographic waves.

4. The power and electronic control assembly according to claim 2, wherein the power and electronic control assembly is configured to drive the electromagnetic motor of the electromagnetic pointing device so as to move the linear movable pointer of the electromagnetic pointing device, wherein the movement of the linear movable pointer is electronically synchronized by the power and electronic assembly with manual rotation of the worm shaft of the manually-drivable worm drive arrangement, and wherein electronic measurement of the rotational displacement of the worm shaft of the manually-drivable worm drive arrangement by the angle encoder coaxially attached to the worm shaft arrangement is processed by the power and electronic control assembly.

5. A method of producing a linear shadow line in a visualized ultrasonographic field, comprising:

providing the stereotactic positioning guide apparatus according to claim 2;

placing a head of an ultrasound transducer in the ultrasound transducer enclosure of the positioning guide control assembly;

fastenably inserting a proximal anchor of a lock and release lever of the positioning guide assembly in a corresponding slot of the positioning guide control assembly, wherein an insertable block of the lock and release lever is synchronizably inserted in an open horizontal slot of a cylindrical overtube of the positioning guide assembly with the insertion of the proximal anchor of the lock and release lever of the positioning guide assembly in the corresponding slot of the positioning guide control assembly, wherein the insertion of the insertable block of the lock and release lever into the open horizontal slot of the cylindrical overtube of the positioning guide assembly is synchronized to loosen the rotation cylinder connected to the tubular positioning guide of the positioning guide assembly from the cylindrical overtube so as to let the tubular positioning guide of the positioning guide assembly be rotatable;

powering up the positioning guide control assembly;

placing a proximal end of the stereotactic positioning guide apparatus on a skin overlying a tissue object, wherein an undersurface of a base panel of the positioning guide assembly contacts the skin;

ultrasonographically visualizing an area of the tissue object and the tissue object in the visualized ultrasonographic field of a main ultrasonographic machine;

transmitting ultrasonographic waves from the ultrasound transducer across the electromagnetic pointing device to the tissue object; and blocking transmission of a portion of the ultrasonographic waves from the ultrasound transducer passing through the electromagnetic pointing device by the linear movable pointer of the electromagnetic pointing device, wherein a blocked portion of the ultrasonographic waves by the linear movable pointer produces no visible ultrasonographic signal in the visualized ultrasonographic field, and wherein the blocked portion of the ultrasonographic waves by the linear movable pointer is surrounded by transmitted and visible ultrasonographic waves in the visible ultrasonographic field.

6. The stereotactic positioning guide apparatus according to claim 1, wherein the positioning guide assembly further comprises:

the tubular positioning guide, wherein the tubular positioning guide comprises a tubular conduit configured to fixedly join the rotation cylinder of the rotation cylinder assembly at a right angle, wherein the tubular conduit is configured to slidably pass the invasive tubular device therethrough to reach the tissue object, and wherein the tubular positioning guide is configured to rotate about a joint with the rotation cylinder manually driven by the manually-drivable worm drive arrangement of the positioning guide control assembly;

the rotation cylinder assembly, wherein the rotation cylinder assembly comprises the rotation cylinder, a rotation cylinder holder and a nonslip tubular elastomer, wherein the rotation cylinder is configured to be tightly encircled by the nonslip tubular elastomer, wherein the rotation cylinder is configured to coaxially mate with an output shaft of the manually-drivable worm drive arrangement so as to be coaxially rotatable by the output shaft of the manually-drivable worm drive arrangement, wherein the rotation cylinder encircled by the nonslip tubular elastomer is rotatably housed in the rotation cylinder holder, wherein the rotation cylinder holder comprises a cylindrical overtube having an open horizontal slot disposed thereof on the cylindrical overtube, wherein the open horizontal slot is configured to reversibly couple with and to uncouple from the lock and release lever of the positioning guide assembly, and wherein the nonslip tubular elastomer is configured to provide the rotation cylinder and the rotation cylinder holder with circumferential friction so as to concentrically fasten the rotation cylinder by the rotation cylinder holder; and the lock and release lever, wherein the lock and release lever is configured as pivotable rocker switch, wherein the lock and release lever comprises a proximal anchor and an insertable block connected to the proximal anchor, wherein the proximal anchor is configured to be pivotably inserted in a corresponding slot of the positioning guide control assembly so as to reversibly fasten the positioning guide assembly to the positioning guide control assembly, wherein the insertable block is configured to be pivotably inserted in the open horizontal slot of the cylindrical overtube of the rotation cylinder holder to release the rotation cylinder of the rotation cylinder assembly from the cylindrical overtube so as to let the rotation cylinder be rotatable, wherein the pivotable insertion of the proximal anchor in the corresponding slot of the positioning guide assembly is configured to be synchronized with the releasing of the rotation cylinder from the cylindrical overtube by the pivotable insertion of the insertable block in the open horizontal slot, wherein the insertable block is configured to be pivotably released from the open horizontal slot of the cylindrical overtube so as to let the cylindrical overtube concentrically lock the rotation cylinder of the rotation cylinder assembly, and wherein the concentric locking of the rotation cylinder by the cylindrical overtube by the pivotable release of the insertable block from the open horizontal slot of the cylindrical overtube is configured to synchronizably uncouple the positioning guide assembly from the position guide control assembly, a base panel, wherein the base panel comprises a flat wall configured to face a skin of the tissue object, and a pair of vertical attachment bars fixedly connecting the rotation cylinder assembly to the base panel so as to steady the positioning guide assembly during independent operation of the positioning guide assembly for the guiding of the invasive tubular device inside the tubular positioning guide.

7. A method of guiding an invasive tubular device to reach a tissue object in a visualized ultrasonographic field, comprising:

providing a stereotactic positioning guide apparatus comprising a positioning guide assembly and a positioning guide control assembly;

placing a head of an ultrasound transducer in an ultrasound transducer enclosure of the positioning guide control assembly;

fastenably inserting a proximal anchor of a lock and release lever of the positioning guide assembly in a corresponding slot of the positioning guide control assembly, wherein an insertable block of the lock and release lever is synchronizably inserted in an open horizontal slot of a cylindrical overtube of the positioning guide assembly with the insertion of the proximal anchor of the lock and release lever of the positioning guide assembly in the corresponding slot of the positioning guide control assembly, wherein the insertion of the insertable block of the lock and release lever into the open horizontal slot of the cylindrical overtube of the positioning guide assembly is synchronized to loosen the rotation cylinder connected to a tubular positioning guide of the positioning guide assembly from the cylindrical overtube so as to let the tubular positioning guide of the positioning guide assembly be rotatable;

powering up the positioning guide control assembly;

placing a proximal end of the stereotactic positioning guide apparatus on a skin overlying a tissue object, wherein an undersurface of a base panel of the positioning guide assembly contacts the skin;

ultrasonographically visualizing an area of the tissue object and the tissue object in a visualized ultrasonographic field of a main ultrasonographic machine;

manually rotating a worm shaft of the manually-drivable worm drive arrangement of the positioning guide control assembly;

electronically measuring the manual rotation of the worm shaft of the manually-drivable worm drive arrangement by an angle encoder coaxially attached to the worm shaft of the manually-drivable worm drive arrangement;

providing a power and electronic control assembly with an electronic information of the manual rotation of the worm shaft of the manually-drivable worm drive arrangement;

providing an electromagnetic motor of an electromagnetic pointing device of the positioning guide control assembly with an electricity from the power and electronic control assembly based on the electronic information of the manual rotation of the worm shaft of the manually-drivable worm drive arrangement so as to controllably move a linear movable pointer of the electromagnetic pointing device;

synchronizing the manual rotation of the worm shaft of the manually-drivable worm drive arrangement with the movement of the linear movable pointer of the electromagnetic pointing device by the power and electronic control assembly;

continuing to manually rotate the worm shaft of the manually-drivable worm drive arrangement until a linear shadow line in the visual ultrasonographic field produced by the linear movable pointer of the electromagnetic pointing device intersects the tissue object in the visualized ultrasonographic field, wherein the tubular positioning guide is synchronizably rotated about the rotation cylinder of the positioning guide assembly until a longitudinal axis of the tubular positioning guide is aligned with the tissue object, and wherein the intersection of the tissue object by the linear shadow line is coincided with the aligning of the longitudinal axis of the tubular positioning guide with the tissue object;

releasing the proximal anchor of the lock and release lever of the positioning guide assembly from the corresponding slot of the positioning guide control assembly, wherein the insertable block of the lock and release lever is synchronizably released from the open horizontal slot of the cylindrical overtube of the positioning guide assembly with the releasing of the proximal anchor of the lock and release lever of the positioning guide assembly from the corresponding slot of the positioning guide control assembly, wherein the releasing of the insertable block of the lock and release lever from the open horizontal slot of the cylindrical overtube of the positioning guide assembly is synchronized to concentrically lock the rotation cylinder connected to a tubular positioning guide of the positioning guide assembly by the cylindrical overtube;

detaching the positioning guide control assembly from the positioning guide assembly, wherein the undersurface of the base panel of the positioning guide assembly is securely adhered to the skin overlying the tissue object, wherein the tubular positioning guide of the positioning guide assembly is immovably aligned with the tissue object in a way the longitudinal axis of the tubular positioning guide intersects said tissue object at an angle so as to direct an invasive tubular device to the tissue object through the tubular positioning guide, and wherein the base panel of the positioning guide assembly is configured to allow the invasive tubular device to pass therethrough to the tissue object.

* * * * *